United States Patent
Stahmann et al.

(10) Patent No.: US 8,523,771 B2
(45) Date of Patent: Sep. 3, 2013

(54) CARDIOVASCULAR PRESSURE ANNOTATIONS AND LOGBOOK

(75) Inventors: Jeffrey E. Stahmann, Ramsey, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1260 days.

(21) Appl. No.: 11/674,031

(22) Filed: Feb. 12, 2007

(65) Prior Publication Data
US 2008/0195165 A1 Aug. 14, 2008

(51) Int. Cl.
*A61B 5/02* (2006.01)

(52) U.S. Cl.
USPC ............ 600/301; 600/483; 600/485; 600/486

(58) Field of Classification Search
USPC .................................. 600/301, 483, 485–486
See application file for complete search history.

(56) References Cited

U.S. PATENT DOCUMENTS

| | | | |
|---|---|---|---|
| 4,686,987 A | 8/1987 | Salo et al. | |
| 5,187,657 A * | 2/1993 | Forbes .......................... | 600/513 |
| 5,284,136 A | 2/1994 | Hauck et al. | |
| 6,076,015 A | 6/2000 | Hartley et al. | |
| 6,666,826 B2 | 12/2003 | Salo et al. | |
| 6,970,742 B2 | 11/2005 | Mann et al. | |
| 2002/0026122 A1 * | 2/2002 | Lee et al. ...................... | 600/523 |
| 2002/0143262 A1 * | 10/2002 | Bardy ........................... | 600/508 |
| 2003/0144595 A1 * | 7/2003 | Lade .............................. | 600/485 |
| 2004/0147969 A1 | 7/2004 | Mann et al. | |
| 2005/0080348 A1 * | 4/2005 | Stahmann et al. ............ | 600/529 |
| 2005/0136385 A1 | 6/2005 | Mann | |
| 2005/0137626 A1 * | 6/2005 | Pastore et al. ..................... | 607/3 |
| 2005/0165456 A1 | 7/2005 | Mann | |
| 2005/0182308 A1 * | 8/2005 | Bardy ........................... | 600/300 |
| 2005/0197674 A1 | 9/2005 | McCabe et al. | |
| 2005/0288596 A1 | 12/2005 | Eigler | |
| 2005/0288604 A1 | 12/2005 | Eigler | |
| 2005/0288722 A1 | 12/2005 | Eigler et al. | |
| 2006/0009737 A1 | 1/2006 | Whiting | |
| 2006/0009810 A1 | 1/2006 | Mann et al. | |
| 2006/0041281 A1 * | 2/2006 | Von Arx et al. ................. | 607/18 |
| 2006/0074398 A1 | 4/2006 | Whiting et al. | |
| 2006/0079769 A1 | 4/2006 | Whiting et al. | |
| 2006/0079787 A1 | 4/2006 | Whiting et al. | |
| 2006/0116593 A1 | 6/2006 | Zhang et al. | |
| 2006/0149324 A1 | 7/2006 | Mann et al. | |
| 2006/0149330 A1 | 7/2006 | Mann et al. | |
| 2006/0149331 A1 | 7/2006 | Mann et al. | |

OTHER PUBLICATIONS

"Arrhythmia Logbook", *System Guide*—Contak Renewal(r) 3 (Models H170/H175) / Contak Renewal(r) 3 HE (Models H177/H179), (Guidant Corporation, St. Paul, MN),(2004), 7-5-7-13.

Kane, et al., "Implantable Medical Device With Chemical Sensor and Related Methods", U.S. Appl. No. 11/383,933, filed May 17, 2006, 68 pgs.

* cited by examiner

*Primary Examiner* — Nicole F Lavert

(74) *Attorney, Agent, or Firm* — Schwegman Lundberg & Woessner, P.A.

(57) ABSTRACT

A system comprises an external medical device configured to communicate with a first implantable medical device (IMD). The external medical device includes a communication circuit and a display. The communication circuit is configured to receive information associated with cardiovascular pressure from the IMD. The external medical device is configured to annotate a waveform on the display to indicate one or more events associated with cardiovascular pressure.

22 Claims, 6 Drawing Sheets

CARDIOVASCULAR PRESSURE ANNOTATIONS AND LOGBOOK

FIELD OF THE INVENTION

The field generally relates to implantable medical devices and, in particular, but not by way of limitation, to systems and methods for monitoring a hemodynamic parameter of a subject.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring one or more electrical heart activity signals. In addition to electrical events, CFM devices may measure and monitor one or more hemodynamic parameters related to heart chamber filling or contraction. These parameters may provide an indication of the metabolic need of a patient for a particular level of cardiac output, for example. The parameters may be useful to track the progression of disease, such as congestive heart failure, for example. Measuring and monitoring the parameters may also be useful to detect a sudden episode such as acute myocardial ischemia. As technology used in IMDs increases, the devices are able to collect data from multiple types of sensors. However, this can complicate the task of data management for caregivers.

SUMMARY

This document relates generally to systems, devices, and methods for assessing the metabolic demand of a patient as indicated through cardiovascular pressure. A system example includes an external medical device configured to communicate with an implantable medical device (IMD). The external medical device includes a communication circuit and a display. The communication circuit is configured to receive information associated with cardiovascular pressure from the IMD. The external medical device is configured to annotate a waveform on the display to indicate one or more events associated with cardiovascular pressure.

Another system example includes an IMD. The IMD includes an implantable cardiovascular pressure sensor interface unit, an implantable cardiac signal sensing circuit, a memory, and a trigger detector. The trigger detector is coupled to the cardiovascular pressure interface unit, the implantable cardiac signal sensing circuit, and the memory. The cardiovascular pressure interface unit is configured to receive a sensor signal associated with cardiovascular pressure of a subject. The implantable cardiac signal sensing circuit is configured to receive at least one sensed intrinsic heart signal from at least one implantable electrode. The trigger detector is configured to store at least one of cardiovascular pressure sensor signal data and detected cardiovascular pressure-related event annotations in response to a triggering event detected from a sensed electrical cardiac signal.

A method example includes communicating information associated with cardiovascular pressure from an IMD to an external device, and annotating a displayed waveform on the external device to indicate one or more detected events associated with cardiovascular pressure.

Another method example includes sensing one or more cardiac signals representative of intrinsic cardiac activity of a subject using an IMD, sensing cardiovascular pressure of the subject, and storing at least one of sampled cardiovascular pressure sensor signal data and detected cardiovascular pressure-related event annotations in the IMD in response to a detected triggering event detected from a sensed cardiac signal.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
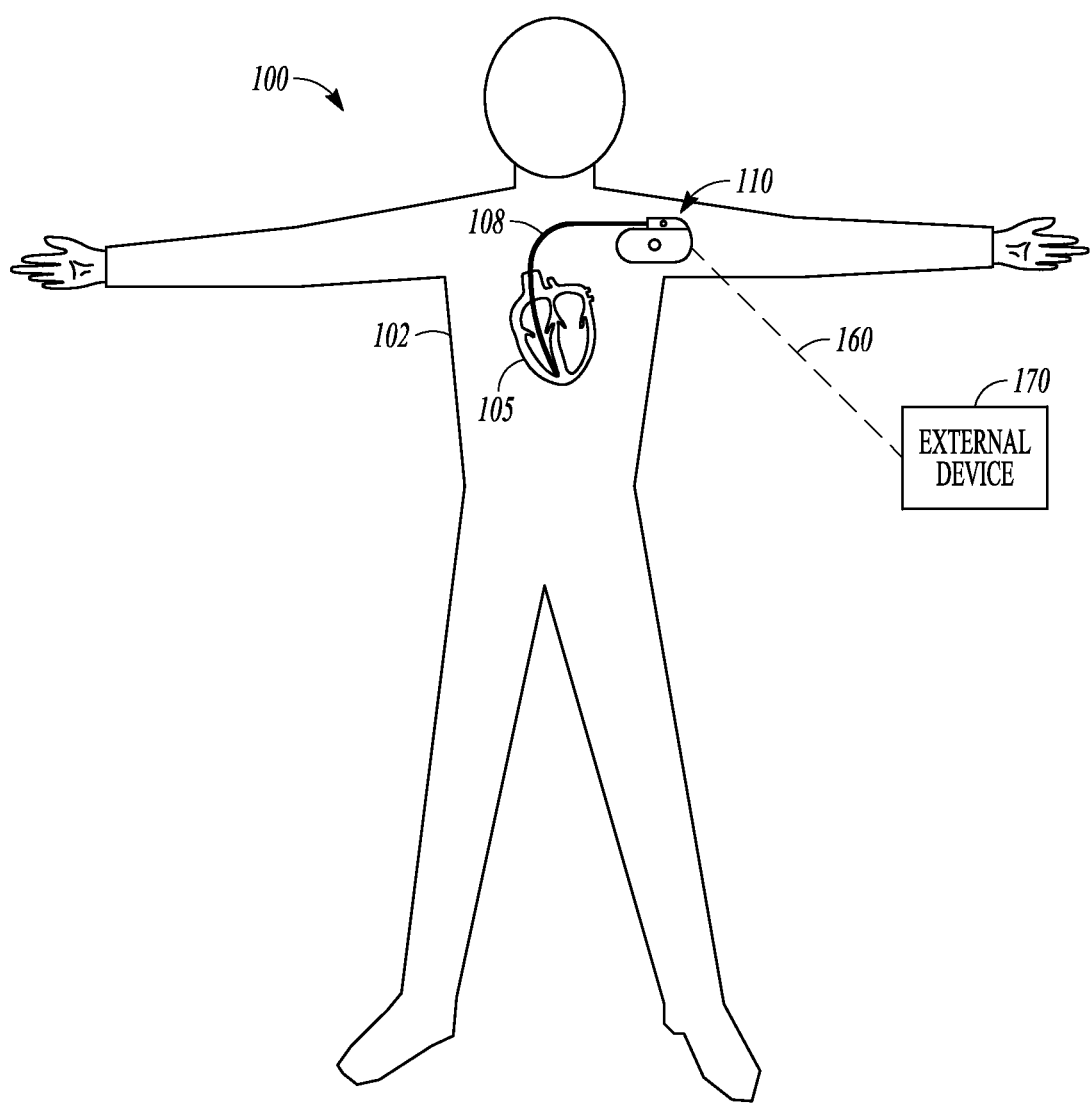
FIG. 1 is a block diagram of portions of a system that uses an IMD.

FIG. 1 is a block diagram of portions of a system 100 that uses an implantable medical device (IMD) 110. As one example, the system 100 shown is used to treat a cardiac arrhythmia. The IMD 110 typically includes an electronics unit coupled by a cardiac lead 108, or additional leads, to a heart 105 of a patient 102 or subject, or otherwise associated with the heart 105. Examples of IMD 110 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. System 100 also typically includes an IMD programmer or other external device 170 that communicates one or more wireless signals 160 with the IMD 110, such as by using radio frequency (RF) or one or more other telemetry methods.

Cardiac lead 108 includes a proximal end that is coupled to IMD 110 and a distal end, coupled by one or more electrodes to one or more portions of a heart 105. The electrodes typically deliver cardioversion, defibrillation, pacing, or resynchronization therapy, or one or more combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the one or more electrodes disposed on or around a heart 105. The lead 108 or leads and electrodes are also typically used for sensing intrinsic or other electrical activity of the heart 105.

An IMD 110 may include one or more of the features, structures, methods, or combinations thereof described herein. For example, a cardiac monitor or a cardiac stimulator may be implemented to include one or more of the described features and processes. It is intended that such a monitor, stimulator, or other implantable or partially implantable device need not include all of the features described herein, but may be implemented to include one or more selected features that may provide one or more unique structures or functionality. Such a device may be implemented to provide a variety of therapeutic or diagnostic functions.

Figure 2:
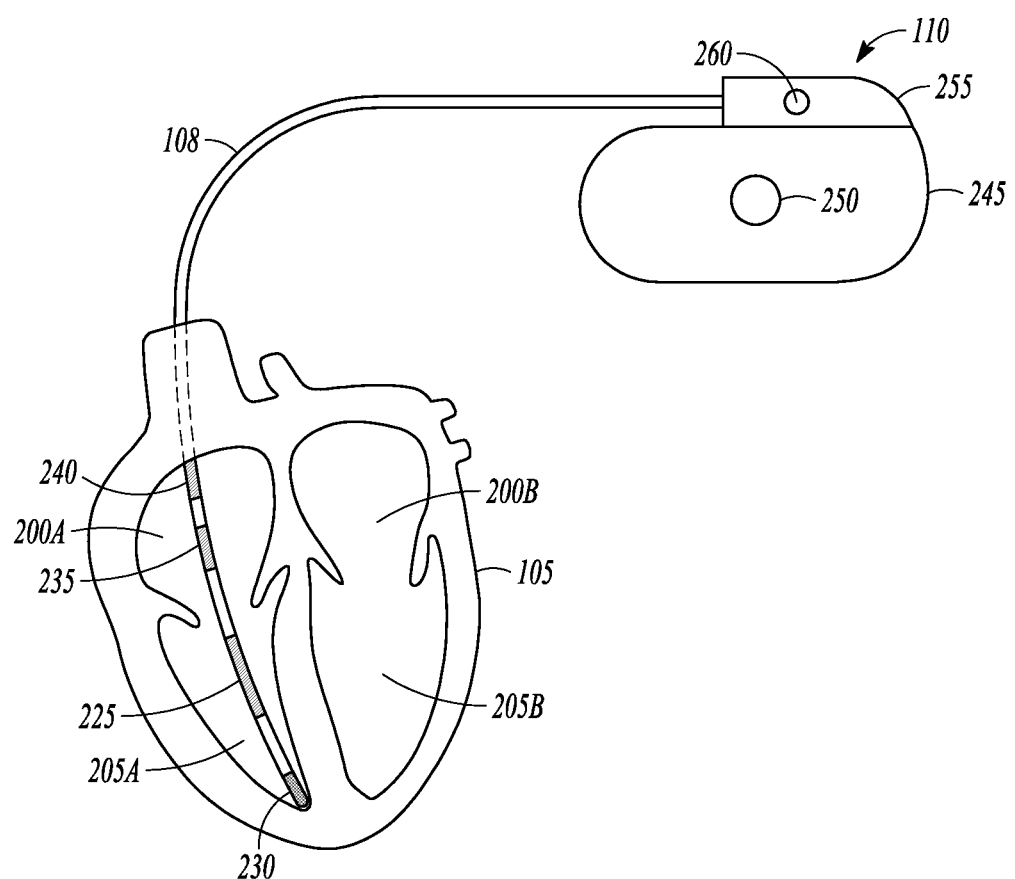
FIG. 2 illustrates an IMD coupled by one or more leads to a heart.

FIG. 2 illustrates an IMD 110 coupled by one or more leads 108 to heart 105. Heart 105 includes a right atrium 200A, a left atrium 200B, a right ventricle 205A, and a left ventricle 205B. In this example, the lead 108 includes one or more electrodes (electrical contacts, such as ring electrode 225 and tip electrode 230) disposed in a right ventricle 205A of heart 105 for sensing one or more intrinsic signals, or delivering pacing therapy, or both, to the right ventricle 205A. In this example, the lead 108 also includes one or more electrodes configured for placement in the right atrium 200A, such as ring electrode 235 and ring electrode 240, for sensing one or more intrinsic electrical cardiac signals, delivering pacing therapy, or both sensing signals and delivering pacing therapy. Sensing and pacing allows the IMD 110 to adjust timing of the heart chamber contractions. For example, IMD 110 can adjust the timing of ventricular contractions with respect to the timing of atrial contractions delay by sensing a contraction in the right atrium 200A and pacing the right ventricle 205A at the desired atrial-ventricular (AV) delay time. The IMD also includes can or housing electrode 250 formed on the IMD can or housing 245, and header electrode 260 formed on the IMD header 255.

The IMD 110 optionally also includes additional leads or electrodes, such as for delivering atrial cardioversion, atrial defibrillation, ventricular cardioversion, ventricular defibrillation, or one or more combinations thereof to heart 105. Optionally, IMD 110 includes an additional cardiac lead that includes ring electrodes for placement in a coronary vein extending along a wall of the left ventricle 205B. A lead placed in the left ventricle 205B and a lead placed in the right ventricle 205A may be used to optionally provide resynchronization therapy to the heart 105. Defibrillation electrodes typically have larger surface areas than pacing electrodes in order to handle the larger energies involved in defibrillation. Other forms of electrodes include meshes and patches, which may be applied to one or more portions of heart 105, or which may be implanted in one or more other areas of the body to help "steer" electrical current produced by IMD 110. The IMDs may be configured with a variety of electrode arrangements, including transveous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes).

Cardiovascular pressure includes right atrial pressure, left atrial pressure, right ventricular pressure, left ventricular pressure, venous pressure, mixed venous pressure, central venous pressure, peripheral venous pressure, pulmonary venous pressure, and pulmonary arterial pressure. Pulmonary arterial (PA) pressure includes the pressure within a pulmonary artery due to blood leaving the right ventricle through the pulmonary valve and going to the lungs.

Measurements relating to cardiovascular pressure can provide valuable information in assessing the hemodynamic health of a patient or subject. For example, knowledge of a subject's cardiovascular pressure is useful in diagnosing pulmonary hypertension, congestive heart failure (CHF), or heart failure (HF) decompensation. A cardiovascular pressure sensor is able to generate a signal representative of cardiovascular pressure. As an example, a PA pressure sensor may be implanted inside either the right or left branch of the pulmonary artery.

Figure 3:
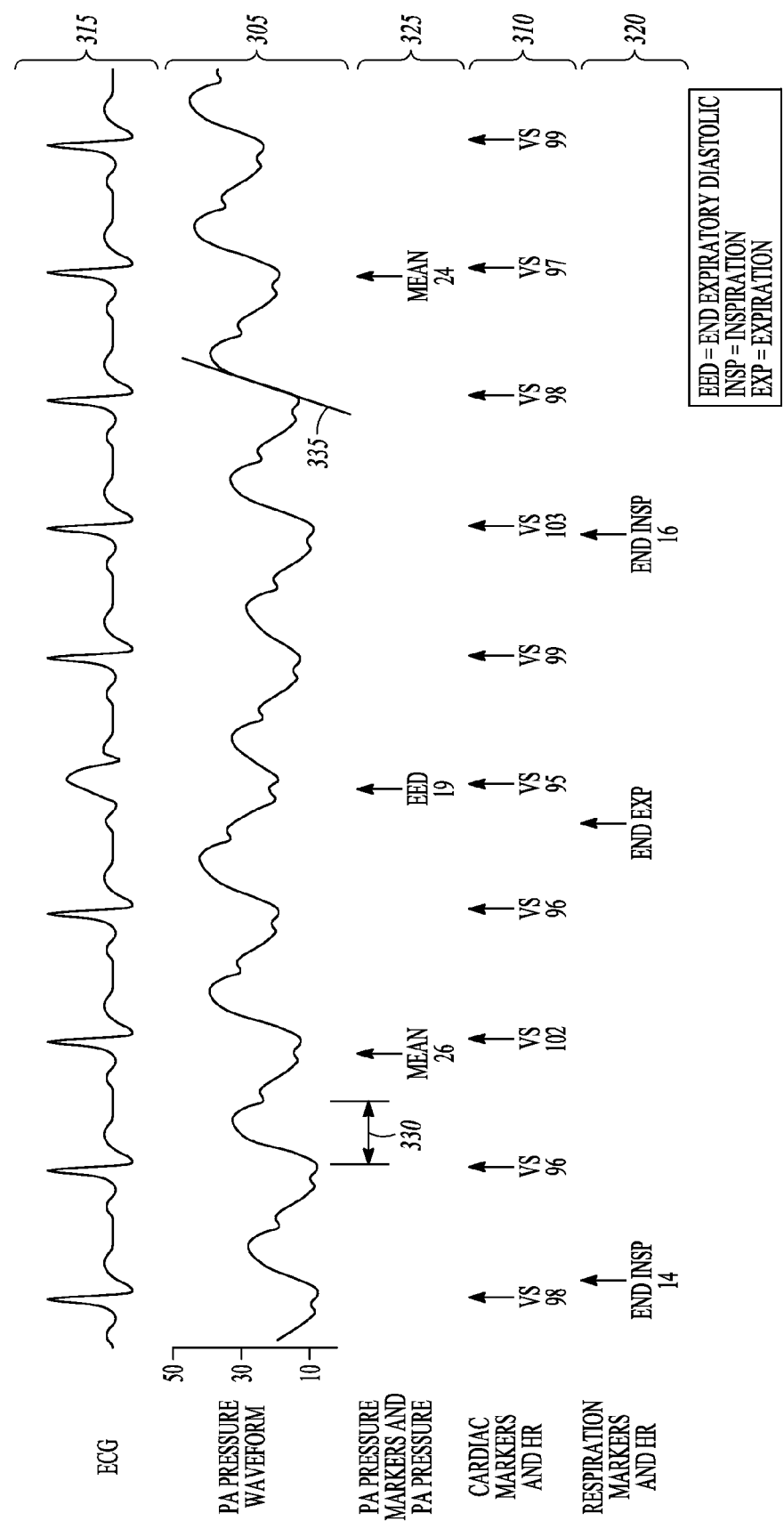
FIG. 3 shows an example of a representation of a cardiovascular pressure waveform obtained from a pulmonary artery pressure sensor signal.

FIG. 3 shows an example of a representation of a cardiovascular pressure waveform 305. The cardiovascular waveform 305 is an example of a pulmonary arterial (PA) pressure waveform obtained from a pulmonary artery pressure sensor signal. In some examples, the cardiovascular pressure waveform 305 is displayed using a strip chart recorder. In some examples, the cardiovascular pressure waveform is displayed using an electronic display. The cardiovascular pressure waveform 305 may be displayed in real time (e.g., substantially as a cardiovascular pressure sensor provides the cardiovascular pressure signal), or the cardiovascular pressure waveform 305 may be stored and later replayed. Adding one or more annotations to a display of cardiovascular pressure will aid a caregiver in interpreting the displayed waveform.

FIG. 3 also shows examples of such annotations. The cardiovascular pressure waveform 305 may be displayed together with one or more R-wave markers 310 annotating the temporal location of an R-wave of the QRS complex of an ECG. The R-wave markers 310 can indicate an R-wave and whether the associated ventricular contraction is a sensed event (VS) or a paced event (VP). The R-wave is only an example of an ECG fiducial mark that may be indicated; one or more other fiducial marks may also be indicated. For example, any part of the P-QRS-T complex may be indicated by a marker. The R-wave markers 310 shown can also indicate heart rate. ECG markers such as R-wave markers 310 are especially useful in situations where the electrocardiogram (ECG) waveform 315 is not displayed. Cardiac arrhythmias may also be indicated by one or more corresponding markers.

The cardiovascular pressure waveform 305 may be displayed concurrently with one or more waveforms or annotations from one or more other implantable or external sensors. Examples include, among other things, one or more cardiac electrograms, information from an activity sensor, a posture sensor, a blood gas sensor, a blood chemical sensor, a blood flow sensor, or a respiration sensor. Presenting visually coherent data from one or more other sensors, such as the ECG waveform 315, may significantly improve the diagnostic value of the cardiovascular pressure waveform 305.

In some examples, the annotations include one or more respiration markers 320. Respiration (breathing) of the subject may modulate the cardiovascular pressure signal. The cardiovascular pressure waveform 305 shown in FIG. 3 shows a PA pressure stroke component modulated by a respiration component. The respiration markers 320 can indicate the end of expiration ("END EXP") and the end of inspiration ("END INSP") of the subject. The respiration markers 320 may also indicate the respiration rate (RR) of the subject. The respiration markers 320 may help a caregiver to interpret the respiration modulation of the cardiovascular pressure waveform 305, but they are especially useful if the respiratory modulation of cardiovascular pressure is removed, such as by processing the cardiovascular pressure signal with a high-pass filter.

In some examples, the annotations include one or more cardiovascular pressure markers 325. A cardiovascular pressure marker 325 may include one or more of a cardiovascular pressure parameter value or a cardiovascular pressure event such as an end expiratory diastolic (EED) value, an end expiratory systolic pressure, a systolic time interval, a rate of change of cardiovascular pressure (dP/dt), a PA pulse pressure, a heart rate, or a central tendency of the cardiovascular pressure such as the mean cardiovascular pressure.

The end expiratory diastolic value of cardiovascular pressure is typically measured after exhaling but just before inhaling. This value may be measured in synchronization with a specified portion of an ECG signal or a respiration signal, or both. The value can also be measured at a valley of the cardiovascular pressure stroke component. During the systolic time interval, the ventricles of the heart are contracting between the closing of the mitral valve and the closing of the aortic valve. The systolic time interval 330 can be determined from an upswing time in a cardiovascular pressure signal (e.g., the time from when cardiovascular pressure starts to increase until the cardiovascular pressure stops increasing).

The rate of change of cardiovascular pressure may be measured on an upstroke of the cardiovascular pressure stroke component during systole, such as the slope 335 in FIG. 3. The rate of change of cardiovascular pressure may be measured in millimeters of mercury per unit time (mmHg/Δt). PA pulse pressure can be thought of as a measure of a difference between systolic and diastolic cardiovascular pressure, and is typically measured at the end of expiration. Cardiovascular pressure, such as PA pressure, can also be used to indicate heart rate, such as by measuring an interval between peaks of the cardiovascular pressure waveform 305.

The annotations can include a value of the mean or other measure of central tendency of the cardiovascular pressure signal. The value of the mean of the cardiovascular pressure may be calculated using one or more weighted or unweighted combinations of diastolic and systolic cardiovascular pressure. For example, the mean of the cardiovascular pressure can be calculated using two diastolic pressure readings (D) and one systolic pressure reading (S), or $$\text{Mean} = \frac{2D + 1S}{3}. \tag{1}$$

The annotations can also include an indication of cardiac arrhythmia, such as determined from values of the cardiovascular pressure signal (e.g., indicative of heart contraction rate) or from a morphology of the cardiovascular pressure signal. For example, a high heart rate may indicate ventricular tachycardia. In another example, if the morphology of the cardiovascular pressure signal becomes substantially flat, this may indicate ventricular fibrillation. In a further example, if the stroke component of a cardiovascular pressure signal is getting pushed higher, this may indicate ventricular tachycardia.

Cardiovascular pressure waveform annotations are useful in patient diagnosis. For example, if a patient or subject is experiencing HF decompensation, left ventricular (LV) filling pressures typically increase. The lungs may couple the higher pressure over to the right ventricle (RV). Because of the difficulties of accessing the LV directly to make a pressure measurement, an accurate indirect measurement may be desirable. Because of the pressure coupling through the lungs, cardiovascular pressure may provide a more accurate reading of this increase in LV filling pressure than an RV measurement. This, in turn, can help diagnose HF decompensation earlier, thereby helping avoid hospitalization costs associated with an undetected or late-detected HF decompensation episode.

Figure 4:
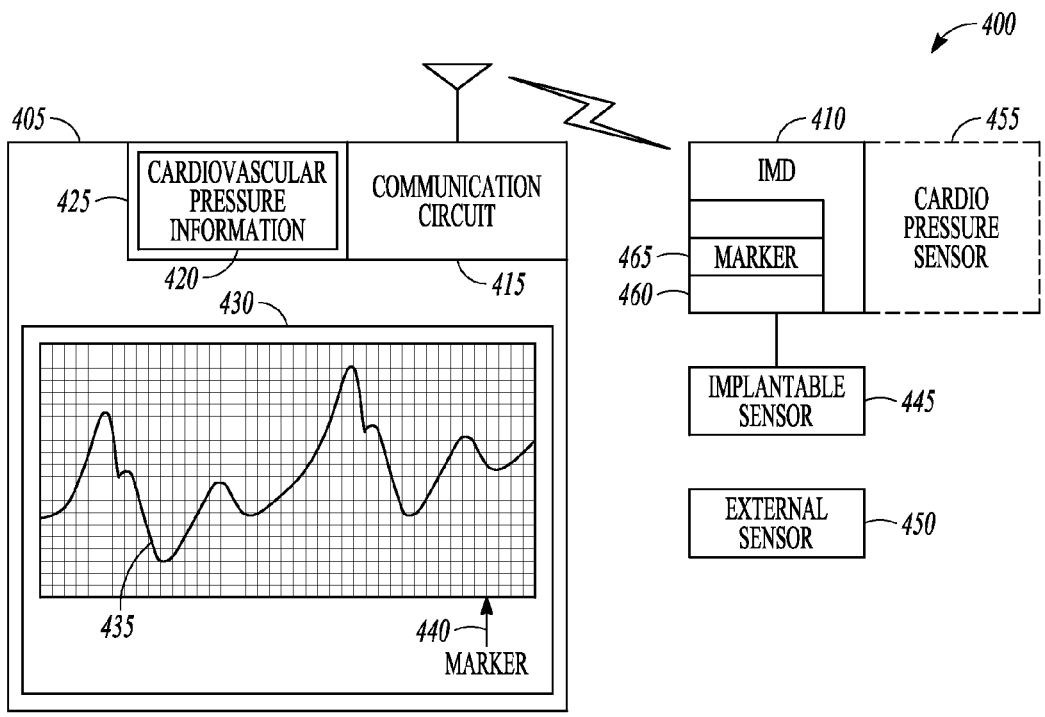
FIG. 4 is a block diagram of portions of an example of a system to monitor cardiovascular pressure of a subject.

FIG. 4 is a block diagram of portions of an example of a system 400 configured to monitor cardiovascular pressure of a subject. In this example, the system 400 includes an external medical device 405 that is configured to communicate with an IMD 410. The external medical device 405 includes a communication circuit 415 that is configured to receive information associated with cardiovascular pressure from the IMD 410. In some examples, the cardiovascular pressure information 420 is received into a memory 425. The external medical device 405 can further include a display 430, such as to display a waveform 435 that is annotated to indicate one or more events associated with cardiovascular pressure. The information includes any pressure and non-pressure information that displayed temporally with cardiovascular pressure.

In some examples, the cardiovascular pressure information 420 received from the IMD 410 includes sampled signal data representative of cardiovascular pressure. The external medical device 405 can display a cardiovascular pressure signal waveform together with at least one cardiovascular pressure marker 440 annotating the displayed cardiovascular pressure waveform to indicate a detected event associated with cardiovascular pressure. The cardiovascular pressure marker 440 may include a cardiovascular pressure parameter value or a cardiovascular pressure event such as an end expiratory diastolic value (EED), end expiratory systolic pressure, systolic time interval, a rate of change of cardiovascular pressure (dP/dt), PA pulse pressure, heart rate, or a central tendency of the cardiovascular pressure such as the mean cardiovascular pressure. The cardiovascular pressure marker 440 may also indicate an episode of cardiac arrhythmia, such as determined by the measured cardiovascular pressure.

In some examples, the external medical device 405 receives sampled signal data representative of at least one intrinsic heart signal from the IMD 410. The external medical device 405 can display an intrinsic heart signal waveform using the sampled signal data together with at least one cardiovascular pressure marker 440. The cardiovascular pressure marker 440 can annotate the intrinsic heart signal waveform to indicate a detected event associated with cardiovascular pressure. In some examples, the external medical device 405 receives both cardiovascular pressure information 420 and information associated with an intrinsic heart signal, and displays a cardiovascular pressure signal waveform and the intrinsic heart signal waveform together with at least one cardiovascular pressure marker 440. The cardiovascular pressure marker 440 annotates at least one of the cardiovascular pressure waveform and the intrinsic heart signal waveform to indicate a detected event associated with cardiovascular pressure. In some examples, the external medical device 405 displays at least one cardiovascular pressure marker 440 indicating a detected event associated with cardiovascular pressure and at least one event marker indicating a detected event associated with sensed intrinsic heart activity.

In some examples, the external medical device 405 receives sampled signal data from the IMD 410 that is representative of at least one second sensor signal produced by a second implantable sensor 445. In some examples, the second implantable sensor 445 is included in the IMD 410. The second sensor signal is related to a physiologic condition of a subject and is different from a cardiovascular pressure sensor. The external medical device 405 displays a cardiovascular pressure signal waveform and a second sensor signal waveform together with at least one cardiovascular pressure marker 440. The cardiovascular pressure marker 440 annotates at least one of the cardiovascular pressure signal waveform and the second sensor signal waveform to indicate an event associated with cardiovascular pressure.

In some examples, the second implantable sensor 445 includes a patient activity sensor. An example of an implantable patient activity sensor includes an accelerometer. In some examples, the second implantable sensor 445 includes a blood gas sensor. An example of a blood gas sensor is an implantable oxygen saturation sensor. An oxygen saturation sensor produces an electrical sensor signal associated with changes in the fluid oxygen saturation. Such changes may occur in association with the heart's mechanical activity, contractility, or blood flow.

In some examples, the second implantable sensor 445 includes a blood chemical sensor. Illustrative examples include a blood electrolyte sensor, such as to detect one or more of potassium (K), sodium (Na) calcium (Ca), glucose, or creatinine. In some examples, a blood chemical sensor detects changes in blood pH. An example of an approach to providing a chemical sensor in a coronary sinus is found in Kane et al., U.S. patent application Ser. No. 11/383,933, entitled, "Implantable Medical Device with Chemical Sensor and Related Methods, filed May 17, 2006, which is incorporated herein by reference.

In some examples, the second implantable sensor 445 includes a blood flow sensor. Examples of a blood flow sensor include a cardiac output sensor circuit or a stroke volume sensor circuit. Examples of stroke volume sensing are discussed in Salo et al., U.S. Pat. No. 4,686,987, "Biomedical Method And Apparatus For Controlling The Administration Of Therapy To A Patient In Response To Changes In Physiologic Demand," filed Mar. 29, 1982, and in Hauck et al., U.S. Pat. No. 5,284,136, "Dual Indifferent Electrode Pacemaker," filed May 13, 1991, which are incorporated herein by reference in their entirety.

In some examples, the second implantable sensor 445 includes a respiration sensor. An example of an implantable respiration sensor is a transthoracic impedance sensor to measure minute respiration volume. An approach to measuring transthoracic impedance is described in Hartley et al. U.S. Pat. No. 6,076,015 "Rate Adaptive Cardiac Rhythm Management Device Using Transthoracic Impedance," filed Feb. 27, 1998, which is incorporated herein by reference.

In some examples, the external medical device 405 is communicatively coupled with at least one external sensor 450. For example, the external sensor 450 may be communicatively coupled via a Universal Serial Bus (USB) or a serial channel, or the external sensor 450 may be communicatively coupled to the external medical device 405 wirelessly. The external sensor 450 produces an external sensor signal associated with a physiologic condition of a subject. For example, the external sensor 450 may be an external ECG device. In certain examples, the external medical device 405 displays the external sensor signal waveform together with at least one cardiovascular pressure marker 440. The cardiovascular pressure marker 440 annotates the external sensor signal waveform to indicate a detected event associated with cardiovascular pressure.

The annotated display of one or more waveforms may also be printed, such as by using a strip chart recorder, for example. In some examples, the external medical device 405 includes a programming device for the IMD 410. In certain examples, the external medical device 405 communicatively coupled to a communication network, such as the internet or a mobile telephone network. The external medical device 405 can communicate with the IMD, such as by using a third device, such as a repeater that is in the same room as the subject, for example.

The annotated display of a cardiovascular pressure waveform together with one or more other waveforms, such as an ECG waveform or a respiration waveform, allows a clinician or caregiver to verify that the IMD 410 is working properly, and is properly interpreting cardiac events (e.g., end diastole) or respiratory events (e.g., end expiration).

Cardiovascular pressure can be affected by the subject's posture. A change in cardiovascular pressure due to a change in posture of a patient may complicate interpretation of one or more events associated with cardiovascular pressure. In some examples, the external medical device 405 receives patient posture information from the IMD 410. For example, the MD 410 may include a posture sensor. In some examples, the cardiovascular pressure information may only be collected while the subject is in a particular posture, such as when the subject is laying down, for example. In some examples, the cardiovascular pressure information may be collected while the subject is in multiple detected postures, and the cardiovascular pressure measurements are binned according to the different postures, or otherwise associated with a particular posture. In addition to lying down, examples of these particular postures may include the subject being upright, laying his or her left side, or laying on his or her right side. In some examples, the cardiovascular pressure measurements may be binned together with or otherwise associated with a corresponding angle of recumbency. The angle of recumbency may be defined according to an orientation of the thorax of the subject, such as with respect to a vertical position, or with respect to a horizontal position.

In certain examples, the external medical device 405 receives the cardiovascular pressure information 420 together with patient posture information. The external medical device 405 can display a cardiovascular pressure signal waveform together with at least one indication of the subject's posture. In some examples, the posture indication may be displayed as at least one recumbency angle (e.g., depending on whether a single axis or multiple axis posture sensor is used).

In some examples, a cardiovascular pressure waveform can be displayed together with an indication that includes one or more figures or icons, such as to graphically indicate the subject's posture. An icon of a patient or subject can be displayed (e.g., with respect to vertical) in a two-dimensional orientation, such superior/inferior and lateral for example. For example, if the patient is standing vertical, as measured by the posture sensor, the icon would show a standing patient. In some examples, the angle of recumbency is a default display setting of the external medical device 405 and the clinician can optionally view a two-dimension orientation such as superior/inferior and posterior/anterior. The external medical device 405 may include a user interface to select between posture indications, such as a graphically-displayed push-button, for example, that enables posture data to be displayed, or that controls the format of how the posture data is displayed.

In some examples, the IMD 410 is configured to sense cardiovascular pressure. For example, the IMD 410 may include an implantable cardiovascular pressure sensor 455, such as an implantable PA pressure sensor for example. In some examples, the IMD 410 receives the cardiovascular pressure information from another device. In some examples, the MD 410 is configured to deliver at least one of bradycardia therapy, tachycardia therapy, or cardiac resynchronization therapy.

As discussed above, the system 400 may include at least one second implantable sensor 445 communicatively coupled to the IMD 410. The second implantable sensor 445 produces a second sensor signal related to a physiologic condition of the patient different from cardiovascular pressure. The IMD 410 may include a memory 460. The memory 460 stores at least one marker 465 indicating at least one detected event associated with cardiovascular pressure in relation to sensor information obtained from the second implantable sensor 445.

Figure 5:
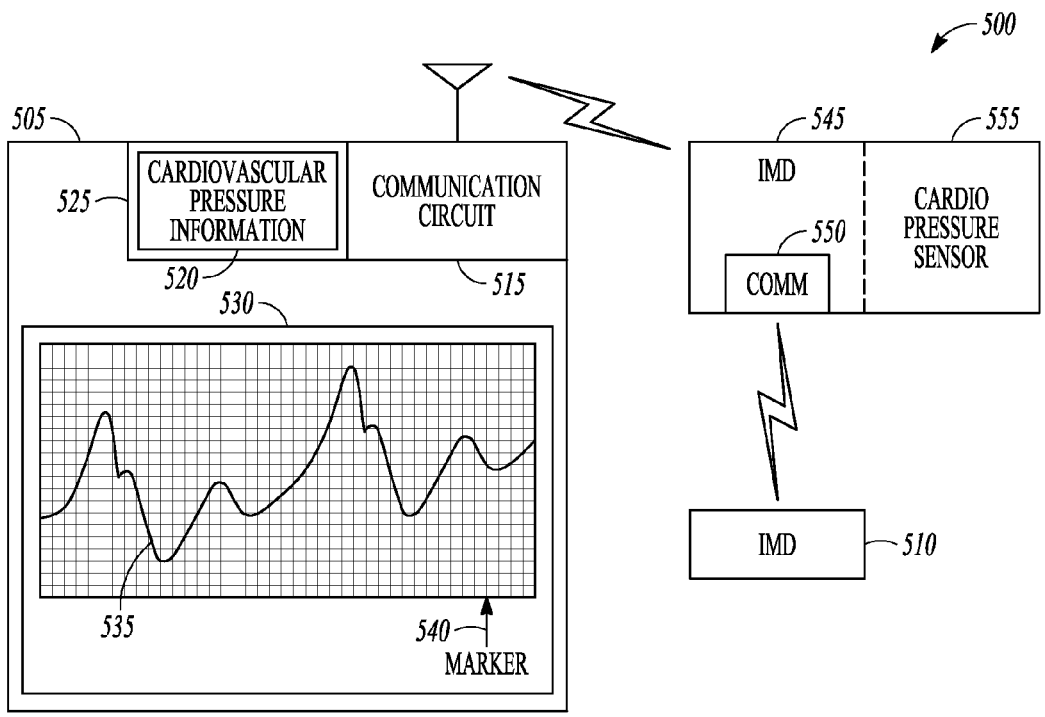
FIG. 5 is a block diagram of portions of another example of a system to monitor cardiovascular pressure of a subject.

FIG. 5 is a block diagram of portions of another example of a system 500 to monitor cardiovascular pressure of a subject. The system 500 includes an external medical device 505 configured to communicate with a first IMD 510. The external medical device 505 includes a communication circuit 515 configured to receive information from the first IMD 510 associated with cardiovascular pressure. In some examples, the information associated with cardiovascular pressure 520 is received into memory 525. The external medical device 505 further includes a display 530. The external medical device 505 displays a waveform 535 that is annotated to indicate one or more events associated with cardiovascular pressure. In some examples, the external medical device 505 annotates a waveform 535 using at least one cardiovascular pressure marker 540 indicating a detected event associated with cardiovascular pressure.

The system further includes a second IMD 545. The second IMD 545 includes a communication circuit 550 and is configured to sense cardiovascular pressure. For example, the second IMD 545 may include an implantable cardiovascular pressure sensor 555. The first IMD 510 is configured to receive information associated with cardiovascular pressure from the second IMD 545.

Figure 6:
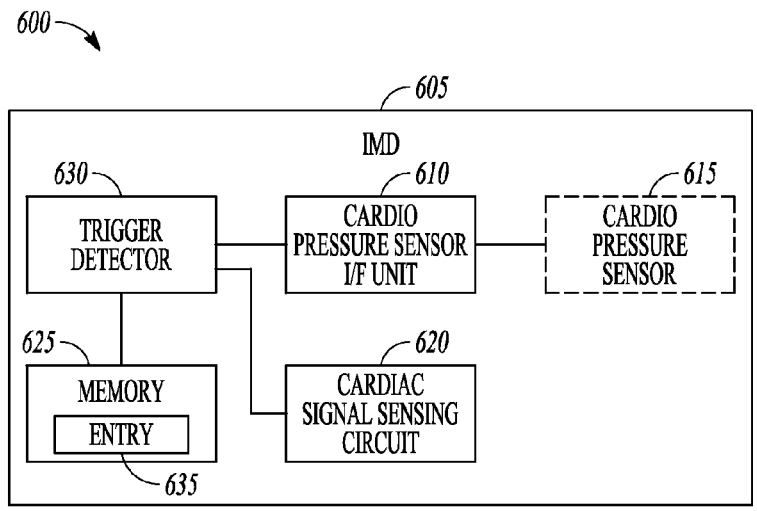
FIG. 6 is a block diagram of portions of another example of a system to monitor cardiovascular pressure of a subject.

FIG. 6 is a block diagram of portions of another example of a system 600 to monitor cardiovascular pressure of a subject. The system 600 includes an IMD 605. The MD 605 includes an implantable cardiovascular pressure sensor interface unit 610. The cardiovascular pressure sensor interface unit 610 receives a sensor signal associated with cardiovascular pressure of a subject. In some examples, the IMD 605 may also include a cardiovascular pressure sensor 615 communicatively coupled to the cardiovascular pressure sensor interface unit 610. In some examples, the cardiovascular pressure sensor 615 includes an implantable PA pressure sensor. The IMD 605 additionally includes an implantable cardiac signal sensing circuit 620. The implantable cardiac signal sensing circuit 620 receives at least one intrinsic heart signal of the subject from at least one implantable electrode.

The IMD further includes a memory 625 and a trigger detector 630 coupled to the cardiovascular pressure interface unit 610, the implantable cardiac signal sensing circuit 620, and the memory 625. The trigger detector 630 stores at least one of cardiovascular pressure sensor signal data or one or more detected cardiovascular pressure-related event annotations in memory 625 in response to a triggering event detected from a sensed electrical cardiac signal. In some examples, the annotations include a cardiovascular pressure marker.

In some examples, the trigger detector 630 stores the cardiovascular pressure signal data or the cardiovascular pressure-related event annotations in memory 625 as a log or logbook. The log may contain information associated with a cardiovascular pressure-related event such as the time and the duration of the event. The cardiovascular pressure signal may be sampled, communicated to the memory, and stored in the log. In some examples, the trigger detector 630 stores an entry 635 in the log in a form that includes at least first and second elements, for example, wherein the first element includes the detected triggering event and the second element includes the sampled signal data or the one or more detected event annotations associated with cardiovascular pressure.

In some examples, the triggering event includes a detected episode of cardiac arrhythmia that triggers storage of the cardiovascular pressure data and detected cardiovascular pressure event annotations. The episode of cardiac arrhythmia may be detected using the implantable cardiac signal sensing circuit 620, or using a received sensor signal associated with cardiovascular pressure, or using both. For example, a high heart rate sensed using the implantable cardiac signal sensing circuit 620 or the received sensor signal associated with cardiovascular pressure may indicate ventricular tachycardia. In another example, the morphology of the sensor signal associated with cardiovascular pressure may indicate ventricular fibrillation or ventricular tachycardia. In some examples, the IMD 605 is configured to deliver at least one of bradycardia therapy, tachycardia therapy, or cardiac resynchronization therapy.

Storing the cardiovascular pressure signal data and the detected event annotations may add diagnostic value to a cardiovascular pressure sensor. Many conditions may be transient and therefore not present during patient evaluation by a clinician. Historical data associated with cardiovascular pressure captured in the log may be useful in patient diagnosis and treatment.

Figure 7:
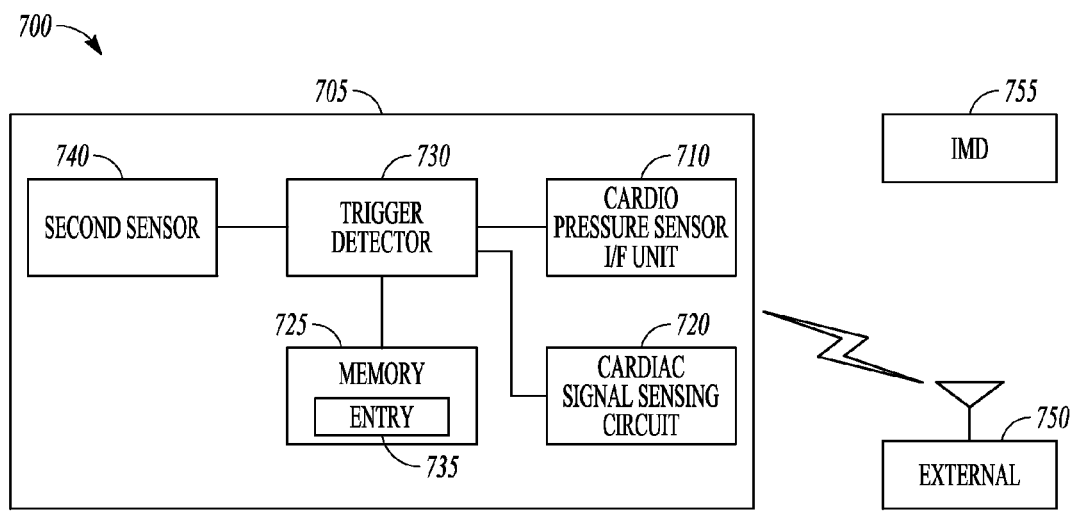
FIG. 7 is a block diagram of portions of another example of a system to monitor cardiovascular pressure of a subject.

FIG. 7 is a block diagram of portions of another example of a system 700 to monitor cardiovascular pressure of a subject. In this example, the system 700 includes an IMD 705. The IMD includes an implantable cardiovascular pressure sensor interface unit 710, an implantable cardiac signal sensing circuit 720, a memory 725, and a trigger detector 730 coupled to the cardiovascular pressure sensor interface unit 710, the implantable cardiac signal sensing circuit 720, and the memory 725. The IMD 705 also includes a second sensor 740. The second sensor 740 produces a second sensor signal associated with a patient's physiologic condition that is different from cardiovascular pressure. Examples of the second sensor can include any of the sensors discussed herein.

The trigger detector 730 stores at least one of cardiovascular pressure sensor signal data or detected cardiovascular pressure-related event annotations in memory 725, such as in response to a triggering event. In some examples, the triggering event includes a detected episode of cardiac ischemia, such as may be detected using any combination of the sensors.

For example, the implantable cardiac signal sensing circuit 720 may provide a wireless ECG. A wireless ECG is a signal approximating the surface ECG and is acquired without using surface (skin contact) ECG electrodes. An example of a circuit for wireless ECG sensing is described in commonly assigned, co-pending U.S. patent application Ser. No. 10/795,126, entitled "WIRELESS ECG IN IMPLANTABLE DEVICES," filed on Mar. 5, 2004, which is incorporated herein by reference. For example, the episode of ischemia may include the subject having an S-wave to T-wave ("ST") interval of the ECG that is elevated, such as by a specified amount from an ST interval of a baseline ECG. The episode of ischemia may also include a change in cardiovascular pressure. The trigger detector 730 stores at least one of cardiovascular pressure sensor signal data or one or more detected cardiovascular pressure-related event annotations in memory 725, for example, as a log entry 735 in response to the detected episode of ischemia. The trigger detector 730 may also store data associated with a signal from the implantable cardiac signal sensing circuit 720.

The trigger detector may also store the triggering event detected using the wireless ECG. An example of a wireless ECG-based ischemia detector is discussed in commonly assigned, co-pending U.S. patent application Ser. No. 11/079,744, entitled "CARDIAC ACTIVATION SEQUENCE MONITORING FOR ISCHEMIA DETECTION," filed on Mar. 14, 2005, which is incorporated herein by reference. In some examples, the second sensor 740 includes a physical activity sensor, such as an accelerometer. The log entry 735 may include information associated with the activity or exertion of the patient, such as deduced from the activity sensor signal.

In some examples, the second sensor 740 includes a posture sensor. The trigger detector can begin storing the data and one or more detected event annotations in response to a detected episode of patient syncope, or fainting. The trigger detector 730 can detect syncope using at least the posture sensor signal, triggering storage of the cardiovascular pressure information as a log entry in memory 725. The trigger detector 730 may also store posture sensor signal related data.

In some examples, the trigger detector 730 can begin storing the data or one or more detected event annotations in response to a detected episode of postural hypotension. Postural hypotension may be detected using the posture sensor and a change in cardiovascular pressure. If the trigger detector 730 detects a change in cardiovascular pressure that exceeds a specified threshold change when a subject is changing posture, such as while a patient is moving to a vertical or upright posture, the trigger detector stores cardiovascular pressure information as a log entry 735 in memory 725.

In some examples, the second sensor 740 includes a respiration sensor. The trigger detector 730 can begin storing the data or one or more detected event annotations in response to a detected episode of disordered breathing. Examples of disordered breathing include, among other things, apnea, hypopnea, periodic breathing, Cheynes-Stokes respiration, and tachypnea. In some examples, the second sensor 740 includes a magnetic field sensor, such as a reed switch. The trigger detector 730 can begin storing the data or one or more detected event annotations in response to a detected magnetic field, such as by a patient placing a magnet near the IMD 705. This allows patient-triggered storage of the data or one or more detected event annotations, such as in response to the patient experiencing a symptom causing the patient concern.

In some examples, the system 700 includes an external device 750 configured such that it is configured to communicate with the IMD 705. The IMD 705 can communicate a log entry 735 from the memory 725 to the external device 750. In some examples, the external device 750 includes a repeater, for example, that is near the subject and that communicates wirelessly with the IMD 705. The repeater can communicate over a communications or computer network, such as to a remote server, thereby placing the remote server in communication with the IMD 705 over the network.

In some examples, the system 700 includes a second IMD 755 that is configured to sense cardiovascular pressure. The second IMD 755 is typically communicatively coupled to the first IMD 705, and provides a sampled cardiovascular pressure signal to the cardiovascular pressure sensor interface unit 710 of the first IMD 705. In some examples, at least one of the first IMD 705 and the second IMD 755 is configured to deliver at least one of bradycardia therapy, tachycardia therapy, or cardiac resynchronization therapy.

Figure 8:
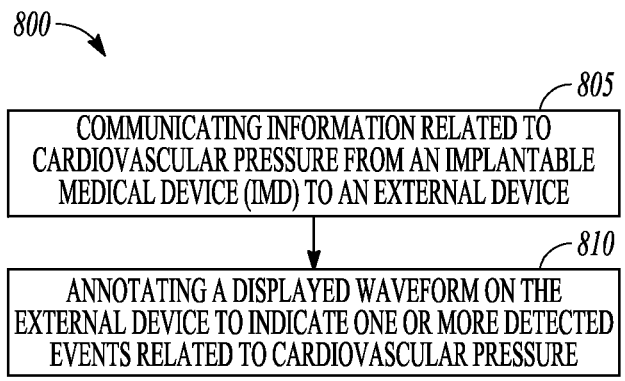
FIG. 8 shows an example of a flow diagram of a method to monitor cardiovascular pressure of a subject.

FIG. 8 shows an example of a flow diagram of a method 800 to monitor cardiovascular pressure of a subject. At 805, information associated with cardiovascular pressure is communicated from an implantable medical device (IMD) to an external device. At 810, a displayed waveform is annotated on the external device, such as to indicate one or more detected events associated with cardiovascular pressure. The cardiovascular pressure waveform may be obtained from cardiovascular pressure sensor.

In some examples, the one or more annotations displayed with the cardiovascular pressure waveform include one or more ECG annotations. The cardiovascular pressure waveform may be displayed with ECG markers or an ECG waveform, or both. The ECG annotations may include an indication of cardiac arrhythmia. In some examples, the method 800 includes displaying one or more respiration annotations with a cardiovascular pressure waveform. Respiration annotations may include an end of expiration annotation, an end of inspiration annotation, or a respiration rate annotation. In some examples, one or more annotations displayed with the cardiovascular pressure waveform include one or more posture indications. The cardiovascular pressure waveform can be displayed together with at least one indication of patient posture.

In some example, a cardiovascular pressure signal waveform is displayed together with at least one cardiovascular pressure marker annotating the cardiovascular pressure waveform to indicate a detected event associated with cardiovascular pressure. A cardiovascular pressure marker may include a cardiovascular pressure parameter value or information about a particular cardiovascular pressure event such as an end expiratory diastolic value (EED), end expiratory systolic pressure, systolic time interval, a rate of change of cardiovascular pressure (dP/dt), PA pulse pressure, heart rate, or a central tendency of the cardiovascular pressure, such as the mean cardiovascular pressure.

In some examples, the method 800 includes displaying a second sensor signal together with at least one indication of one or more detected events associated with cardiovascular pressure. The second sensor signal is produced by a second sensor that is associated with a patient's physiologic condition that is different from cardiovascular pressure. Examples of signal sensed by a the second sensor include an intrinsic heart signal, a patient activity signal, a blood gas sensor signal, a blood chemical sensor signal, a blood flow sensor signal, or a respiration signal.

Figure 9:
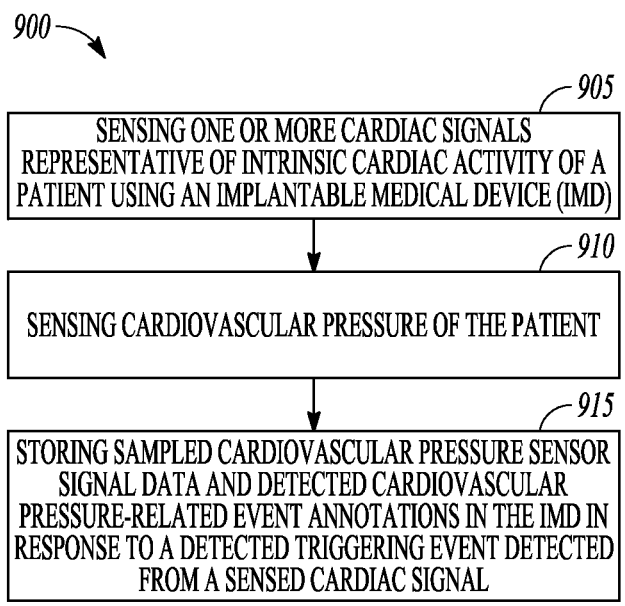
FIG. 9 shows another example of a flow diagram of a method to monitor cardiovascular pressure of a subject.

FIG. 9 shows another example of a flow diagram of a method 900 to monitor cardiovascular pressure of a subject. At 905, one or more cardiac signals representative of intrinsic cardiac activity of a patient are sensed using an IMD. The IMD may include an intrinsic cardiac signal sensing circuit, such as to sense one or more cardiac electrograms, for example.

At 910, a cardiovascular pressure of a subject is sensed. In some examples, the IMD includes a cardiovascular pressure sensor. In some examples, the IMD receives the cardiovascular pressure sensor signal from a second device.

At 915, at least one of sampled cardiovascular pressure sensor signal data or one or more detected cardiovascular pressure-related event annotations are stored in the IMD, such as in response to a detected triggering event detected from a sensed cardiac signal. In some examples, the data and annotations are stored in a log, for example, included in IMD memory. In some examples, the method 900 includes storing in the log at least one entry having at least a first element that includes the detected triggering event and a second element that includes at least one of the sampled cardiovascular pressure sensor signal data or one or more detected cardiovascular pressure-related event annotations.

In some examples, the triggering event includes an episode of a cardiac arrhythmia, and the sampled cardiovascular pressure sensor signal data or one or more detected cardiovascular pressure-related event annotations are stored in response to the IMD detecting the cardiac arrhythmia episode. In some examples, the triggering event includes an episode of cardiac ischemia and the sampled cardiovascular pressure sensor signal data or one or more detected cardiovascular pressure-related event annotations are stored in response to the IMD detecting the cardiac ischemia episode.

In some examples, the sampled cardiovascular pressure sensor signal data and detected one or more cardiovascular pressure-related event annotations are stored in response to the IMD detecting an episode of patient syncope. In some examples, the sampled cardiovascular pressure sensor signal data and one or more detected cardiovascular pressure-related event annotations are stored in response to the IMD detecting an episode of postural hypotension. In some examples, the sampled cardiovascular pressure sensor signal data and one or more detected cardiovascular pressure-related event annotations are stored in response to the IMD detecting an episode of disordered breathing.

In some examples, the triggering event includes the IMD detecting a presence of a magnetic field, such as by the patient placing a magnet near the IMD. The sampled cardiovascular pressure sensor signal data and one or more detected cardiovascular pressure-related event annotations are stored in the log in memory in response to the IMD detecting a presence of a magnetic field. In certain examples, the method 900 can include communicating at least one log entry from the IMD to an external device.

It is to be understood that the above description is intended to be illustrative, and not restrictive. For example, the above-described embodiments (and/or aspects thereof) may be used in combination with each other. As another example, although the above description has emphasized the use of a cardiovascular pressure sensor, in other examples, other blood pressure sensors or signals can be used in conjunction with the various techniques or apparatuses described herein. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
a first implantable medical device (IMD) comprising:
an implantable cardiovascular pressure sensor interface unit, the cardiovascular pressure interface unit configured to receive a sensor signal representative of a pulmonary arterial (PA) pressure of a subject;
an implantable cardiac signal sensing circuit configured to receive at least one intrinsic heart signal from at least one implantable electrode;
a memory; and
a trigger detector coupled to the implantable cardiovascular pressure sensor interface unit, the implantable cardiac signal sensing circuit, and the memory, wherein the trigger detector is configured to:
detect a triggering event from a sensed cardiac signal;
detect one or more PA pressure-associated events in response to the detected triggering event;
store PA pressure sensor signal data and one or more annotations of the one or more detected PA pressure-associated events in response to the detected triggering event, the PA pressure data and the one or more detected PA pressure-associated event annotations stored in temporal association with sensed cardiac signal data, wherein the trigger detector is configured to detect an episode of cardiac arrhythmia using the PA pressure data, the one or more PA pressure-associated event annotations, and the sensed cardiac signal data; and
initiate delivery of device based therapy in response to detecting the episode of cardiac arrhythmia.

2. The system of claim 1, further comprising a PA pressure sensor communicatively coupled to the PA pressure sensor interface unit.

3. The system of claim 1, further comprising a second IMD communicatively coupled to the first IMD, wherein the second IMD is configured to sense cardiovascular pressure.

4. The system of claim 1, wherein the first IMD is configured to deliver at least one of bradycardia therapy, tachycardia therapy, and cardiac resynchronization therapy.

5. The system of claim 1, wherein the trigger detector is configured to begin storing the data and detected event annotations in response to a detected episode of cardiac arrhythmia.

6. The system of claim 1, wherein the trigger detector is configured to begin storing the data and detected event annotations in response to a detected episode of cardiac ischemia.

7. The system of claim 1, wherein the first IMD includes a posture sensor coupled to the trigger detector, and wherein the trigger detector is configured to begin storing the data and detected event annotations in response to a detected episode of patient syncope.

8. The system of claim 1, wherein the first IMD includes a posture sensor coupled to the trigger detector, and wherein the trigger detector is configured to begin storing the data and detected event annotations in response to a detected episode of postural hypotension.

9. The system of claim 1, wherein the first IMD includes a respiration sensor coupled to the trigger detector, and wherein the trigger detector is configured to begin storing the data and detected event annotations in response to a detected episode of disordered breathing.

10. The system of claim 1, wherein the first IMD includes a magnetic field sensor coupled to the trigger detector, and wherein the trigger detector is configured to begin storing the data and detected event annotations in response to a detected magnetic field.

11. The system of claim 1, wherein the trigger detector is configured to store at least one entry in a log that includes at least first and second elements, wherein the first element includes the detected triggering event and the second element includes at least one of sampled signal data and detected event annotations associated with cardiovascular pressure.

12. The system of claim 11, further including an external device configured to communicate with the first IMD, and wherein the first IMD is adapted to communicate at least one log entry to the external device.

13. The system of claim 12, wherein the external device includes a remote server configured to communicate with the first IMD over a communications or computer network.

14. A method of operating an implantable medical device, the method comprising:
   sensing one or more cardiac signals representative of intrinsic cardiac activity of a subject using the IMD;
   sensing a pulmonary arterial (PA) pressure of the subject;
   detecting one or more PA pressure-related events;
   storing sampled PA pressure sensor signal data and one or more annotations of the one or more detected PA pressure-related events in the IMD in response to a detected triggering event detected from a sensed cardiac signal, the PA pressure sensor signal data and the one or more detected PA pressure-associated event annotations stored in temporal association with sensed cardiac signal data; and
   detecting an episode of cardiac arrhythmia using the PA pressure data, the one or more PA pressure-associated event annotations, and the sensed cardiac signal data, and initiating delivery of device-based therapy in response to detecting the episode of cardiac arrhythmia.

15. The method of claim 14, wherein storing includes storing the sampled cardiovascular pressure sensor signal data and detected cardiovascular pressure-related event annotations in response to the IMD detecting an episode of cardiac arrhythmia.

16. The method of claim 14, wherein storing includes storing the sampled cardiovascular pressure sensor signal data and detected cardiovascular pressure-related event annotations in response to the IMD detecting an episode of cardiac ischemia.

17. The method of claim 14, wherein storing includes storing the sampled cardiovascular pressure sensor signal data and detected cardiovascular pressure-related event annotations in response to the IMD detecting an episode of patient syncope.

18. The method of claim 14, wherein storing includes storing the sampled cardiovascular pressure sensor signal data and detected cardiovascular pressure-related event annotations in response to the IMD detecting an episode of postural hypotension.

19. The method of claim 14, wherein storing includes storing the sampled cardiovascular pressure sensor signal data and detected cardiovascular pressure-related event annotations in response to the IMD detecting an episode of disordered breathing.

20. The method of claim 14, wherein storing includes storing the sampled cardiovascular pressure sensor signal data and detected cardiovascular pressure-related event annotations in response to the IMD detecting a presence of a magnetic field.

21. The method of claim 14, wherein storing includes storing at least one entry in a log having at least a first element that includes the detected triggering event and a second element that includes at least one of the sampled cardiovascular pressure sensor signal data and detected cardiovascular pressure-related event annotations.

22. The method of claim 14, further including communicating at least one log entry from the IMD to an external device.

* * * * *